(12) United States Patent
Kothrade et al.

(10) Patent No.: US 6,423,256 B1
(45) Date of Patent: Jul. 23, 2002

(54) PROCESS FOR PRODUCING SOLID DOSAGE FORMS

(75) Inventors: Stephan Kothrade, Limburgerhof; Jörg Breitenbach, Mannheim; Harald Krull, Ludwigshafen; Thomas Kessler, Schifferstadt; Armin Lange, Heidelberg; Werner Maier, Schifferstadt; Ulrich Reinhold, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/417,070

(22) Filed: Oct. 13, 1999

(30) Foreign Application Priority Data

Oct. 15, 1998 (DE) .......................................... 198 47 618

(51) Int. Cl.$^7$ ............................. A61K 9/20; B29C 47/00
(52) U.S. Cl. ....................................... 264/122; 264/211
(58) Field of Search ................................ 264/109, 122, 264/141, 151, 210.2, 331.19, 211, 142, 211.23

(56) References Cited

U.S. PATENT DOCUMENTS

| 4,801,460 A | 1/1989 | Goertz et al. ................ 424/465 |
| 4,880,585 A | 11/1989 | Klimesch et al. ........... 264/141 |
| 4,957,681 A | 9/1990 | Klimesch et al. ........... 264/211 |
| 5,073,379 A | 12/1991 | Klimesch et al. ........... 424/467 |

OTHER PUBLICATIONS

Fikentscher, *Cell. Chemie*, 13, 58–64, 1932.
Sucker et al., *Pharm. Tech.*, 1978.
Ford, *Pharm. Act. Helv*, 61, 69–88, 1986.
Thoma et al., *Pharm. Ind.*, 51, 98–101, 1989.

*Primary Examiner*—Mathieu D. Vargot
(74) *Attorney, Agent, or Firm*—Keil & Weinkauf

(57) ABSTRACT

A process for producing solid dosage forms, in which (i) a plastic mixture of at least one pharmacologically acceptable polymeric binder with a K value of more than 75, at least one pharmaceutical active ingredient and, where appropriate, conventional pharmaceutical additives is prepared and (ii) the plastic mixture is shaped to the required dosage form, with step (i) being carried out under conditions of temperature and shear energy input such that the reduction in molecular weight of the polymeric binder, expressed as the difference in the K value, is less than 15 is described.

8 Claims, No Drawings

PROCESS FOR PRODUCING SOLID DOSAGE FORMS

The invention relates to a process for producing solid dosage forms, in particular solid pharmaceutical dosage forms.

A continuous process for producing solid pharmaceutical forms has been known for some time and entails extruding an active ingredient-containing, solvent-free melt of a polymeric binder, and shaping this extrudate to the required drug form, for example in a calendar with molding rolls, see EP A-240 904, EP-A-240 906, EP-A-337 256 and EP-A-358 105 (melt extrusion). It is possible in this way to achieve specific shaping. Employed as polymeric binder are, in particular, polymers of N-vinylpyrrolidone or copolymers thereof, e.g. with vinyl acetate.

The known process has the disadvantage that polymeric binders with a K value of more than 75, in particular homo- or copolymers of vinylpyrrolidone, cannot be processed because they show crosslinking, discoloration or decomposition at the required temperatures and/or residence times in the extruder. Ancillary substances customary in pharmaceutical technology, such as polyvinylpyrrolidone with a K value of 90, have therefore not been usable to date for producing dosage forms by extrusion. The use of polymeric binders with high K values is of interest for producing solid solutions which permit slow release of active ingredient.

It is an object of the present invention to provide a process for producing solid dosage forms by shaping a plastic mixture which allows high molecular weight polymeric binders to be used.

We have found that this object is achieved by controlling the temperature and the shear energy input during the process.

The present invention therefore relates to a process for producing solid dosage forms, in which (i) a plastic mixture of at least one pharmacologically acceptable polymeric binder with a K value of more than 75, at least one pharmaceutical active ingredient and, where appropriate, conventional pharmaceutical additives is prepared and (ii) the plastic mixture is shaped to the required dosage form, with step (i) being carried out under conditions of temperature and shear energy input such that the reduction in molecular weight of the polymeric binder, expressed as the difference in the K value, is less than 15, preferably less than 10.

Dosage forms mean in this connection all forms suitable for use as drug products, plant treatment products, animal feed products and human food products and for delivering fragrances and perfume oils. These include, for example, tablets of any shape, pellets, granules, but also larger forms such as cubes, blocks (bricks) or cylindrical forms, which can be used, in particular, as animal or human food products.

The dosage forms obtainable according to the invention generally comprise:
a) from 0.1 to 90% by weight, in particular 0.1 to 60% by weight (based on the total weight of the dosage form) of an active ingredient,
b) from 10 to 99.9% by weight, in particular 40 to 99% by weight, of a polymeric binder and
c) where appropriate additives.

The polymeric binder has a K value of more than 75, in particular more than 80, preferably more than 85 and particularly preferably 90–200. The K values are determined by the method of H. Fikentscher, Cellulose-Chemie, volume 13, (1932) 58–64 and 71–74, in aqueous solution or in an organic solvent at 25° C., at concentrations which are between 0.1% and 5% depending on the K value range. The K value of water-soluble polymers is generally determined in aqueous solution. If the polymer is not completely soluble in water, solvents such as THF, acetone, alcohols, e.g. ethanol, are employed.

Step (i) in the process according to the invention is carried out under conditions of temperature and shear energy input such that the reduction in molecular weight of the polymeric binder, expressed as difference in the K value, is less than 15, preferably less than 10. The skilled worker is able easily to establish suitable process parameters on the basis of simple tests. For this purpose, the K value of the polymeric binder in the resulting dosage form is determined and compared with the K value of the polymeric binder employed. The process parameters can be varied so that, while the mixing is adequate, the reduction in molecular weight of the polymeric binder is minimized.

Suitable binders are polymers, copolymers, cellulose derivatives and starch derivatives, for example:

polyvinylpyrrolidone (PVP), copolymers of N-vinylpyrrolidone (NVP) and vinyl acetate or vinyl propionate, copolymers of vinyl acetate and crotonic acid, partially hydrolyzed polyvinyl acetate, polyvinyl alcohol, poly(hydroxyalkyl acrylates), poly (hydroxyalkyl methacrylates), polyacrylates and polymethacrylates (Eudragit types), copolymers of methyl methacrylate and acrylic acid, polyacrylamides, polyethylene glycols, polyvinylformamide (where appropriate partially or completely hydrolyzed), cellulose esters, cellulose ethers, in particular methylcellulose and ethylcellulose, hydroxyalkylcelluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, and mannans, in particular galactomannans. Of these, polyvinylpyrrolidone, copolymers of N-vinylpyrrolidone and vinyl esters, poly(hydroxy alkylacrylates), poly(hydroxyalkyl methacrylates), polyacrylates, polymethacrylates, alkylcelluloses and hydroxyalkylcelluloses are particularly preferred.

Homo- or copolymers of vinylpyrrolidone, in particular those with at least 1% by weight, preferably at least 10% by weight, particularly preferably at least 25% by weight and, in particular, at least 50% by weight of vinylpyrrolidone units, are preferred. Suitable comonomers are vinyl esters of aliphatic $C_2$–$C_{24}$-carboxylic acids, such as vinyl acetate or vinyl propionate; $C_1$–$C_{24}$-alkyl(meth)acrylates, such as methyl methacrylate, ethyl acrylate, stearyl(meth)acrylate; vinyl ethers, such as methyl vinyl ether. Hydrophobic comonomers are generally preferred.

The polymeric binder must soften in the complete mixture of all the components in the range from 70 to 300° C., preferably 80 to 250° C., to form a plastic mixture. The glass transition temperature of the mixture must therefore be below 250° C., preferably below 200° C.

In preferred embodiments, the glass transition temperature is reduced by adding pharmacologically acceptable plasticizing ancillary substances. The amount of plasticizer is generally from 0.5 to 30, preferably 0.5 to 15, % of the total weight of the mixture.

Examples of such plasticizers are:
long-chain alcohols, ethylene glycol, propylene glycol, glycerol, trimethylolpropane, triethylene glycol, butandiols, pentanols, such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol monoacetate, glycerol diacetate or glycerol triacetate or sodium diethyl sulfosuccinate, of which polyethylene glycols and polyethylene/propylene glycols are preferred.

The use of a plasticizer reduces the softening point of the polymeric binder. The formation of the plastic mixture and the shaping can take place at lower temperatures, which limits the reduction in molecular weight.

In preferred embodiments, the plastic mixture also contains pharmaceutically acceptable antioxidants. These can be used in an amount of from 0.001 to 10%, preferably 0.01 to 5%, of the total weight of the mixture. Examples of suitable antioxidants are gallic esters, ascorbyl palmitate, ascorbic acid, butylated hydroxytoluene, butylated hydroxyanisole, tocopherols, nordihydroguajaretic acid, 2,6-di-tert-butyl-4-methylphenol, alkali metal or alkaline earth metal sulfites or bisulfites and mixtures thereof.

The additional use of antioxidants makes it possible to limit further the reduction in molecular weight of the polymeric binder in the process according to the invention.

Examples of conventional pharmaceutical ancillary substances, the total amount of which can be up to 100% of the weight of the polymer, are extenders or bulking agents such as silicates or diatomaceous earth, magnesium oxide, aluminum oxide, titanium oxide, stearic acid or salts thereof, e.g. the magnesium or calcium salt, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % of the total weight of the mixture;

Lubricants such as aluminum, magnesium and calcium stearates, talc and silicones, in a concentration of from 0.1 to 5, preferably 0.1 to 3, % of the total weight of the mixture;

Flow regulators such as animal or vegetable fats, particularly in hydrogenated form and those which are solid at room temperature. These fats preferably have a melting point of 50° C. or above. Triglycerides of $C_{12}$, $C_{14}$, $C_{16}$ and $C_{18}$-fatty acids are preferred. Waxes such as carnauba wax can also be used, these fats and waxes can advantageously be admixed alone or together with mono- and/or diglycerides or phosphatides, in particular lecithin. The mono- and dyglycerides are preferably derived from the abovementioned fatty acid types. The total amount of fats, waxes, mono-, diglycerides and/or lecithins is 0.1 to 30, preferably 0.1 to 5, % of the total weight of the composition for the particular layer;

Dyes such as azo dyes, organic or inorganic pigments or dyes of natural origin, with inorganic pigments in a concentration of from 0.001 to 10, preferably 0.5 to 3, % of the total weight of the mixture being preferred;

Stabilizers such as light stabilizers, hydroperoxide destroyers, radical scavengers, stabilizers against microbial attack.

It is also possible to add wetting agents, preservatives, disintegrants, adsorbants, mold release and blowing agents (see, for example, H. Sucker et al., Pharmazeutische Technologie, Thieme-Verlag, Stuttgart 1978).

Ancillary substances also mean for the purpose of the invention substances for producing a solid solution of the active ingredient. Examples of these ancillary substances are pentaerythritol and pentaerythritol tetraacetate, polymers such as polyethylene oxides and polypropylene oxides and block copolymers thereof (poloxamers), phosphatides such as lecithin, homo- and copolymers of vinylpyrrolidone, surfactants such as polyoxyethylene 40 stearate, and citric and succinic acids, bile acids, sterols and others as indicated, for example, by J. L. Ford, Pharm. Acta Helv. 61, 69–88 (1986).

Ancillary substances are also regarded as being additions of bases and acids to control the solubility of an active ingredient (see, for example, K. Thoma et al., Pharm. Ind. 51, 98–101 (1989)).

The only precondition for suitability of ancillary substances is an adequate thermal stability.

Active ingredients mean for the purpose of the invention all substances with a physiological effect as long as they do not decompose under the processing conditions. They are, in particular, pharmaceutical active ingredients (for humans and animals), active ingredients for treating plants, insecticides, active ingredients for animal and human food products, fragrances and perfume oils. The amount of active ingredient per dose unit and the concentration may vary within wide limits depending on the activity and release rate. The only condition is that they suffice to achieve the desired effect. Thus, the concentration of active ingredient can be in the range from 0.1 to 95, preferably from 20 to 80, in particular from 30 to 70, % by weight. It is also possible to employ combinations of active ingredients. Active ingredients for the purpose of the invention are also vitamins and minerals. These vitamins include the vitamins of the A group, of the B group, meaning not only $B_1$, $B_2$, $B_6$ and $B_{12}$, and nicotinic acid and nicotinicamide, but also compounds with vitamin B properties such as, for example, adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Plant treatment agents include, for example, vinclozolin, epoxiconazole and quinmerac.

The process according to the invention is suitable, for example, for processing the following active ingredients:

acebutolol, acetylcysteine, acetylsalicylic acid, aciclovir, alprazolam, alfacalcidol, allantoin, allopurinol, ambroxol, amikacin, amiloride, amino acetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, chloramphenicol, chlorhexidine, chlor-pheniramine, chlortalidone, choline, cyclosporin, cilastatin, cimetidine, ciprofloxacin, cisapride, cisplatin, clarithromycin, clavulalic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, folinic acid, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, imipramine, indomethacin, iohexol, iopamidol, isosorbide dinitrate, isosorbide mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multi-vitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, pentoxifylline, phenobarbital, phenoxymethylpenicillin, phenylephrine, phenylpropanolamine, phenytoin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, selegiline, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolon-acetonide, triamterene, trimethoprim, troxerutin, uracil, valproic acid, vancomycin, verapamil, vitamin E, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

To produce the solid dosage forms, a plastic mixture of the components is prepared and then subjected to a shaping step. The mixing of the components and the formation of the plastic mixture can take place in various ways. The mixing can take place before, during and/or after the formation of the plastic state. For example, the components can be first mixed and then softened or be mixed and softened simultaneously. If a homogenization of the plastic mixture takes place in order to obtain a thorough dispersion of the active ingredient, this must be carried out under low-shear conditions.

However, it has proven to be preferred, especially on use of sensitive active ingredients, first to soften and premix the polymeric binder, where appropriate together with conventional pharmaceutical additives, and then to mix in (homogenize) the sensitive active ingredient(s) in plastic phase with very short residence times in intensive mixers. The active ingredient(s) can moreover be employed in solid form or as solution or dispersion.

The components are generally employed as such in the production process. However, they can also be used in liquid form, i.e. as solution, suspension or dispersion.

A suitable solvent for the liquid form of the components is primarily water or a water-miscible organic solvent or a mixture thereof with water. However, solvents which can be used are also water-immiscible organic solvents. Suitable water-miscible solvents are, in particular, $C_1$–$C_4$-alkanols such as ethanol, isop-opanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in the particular case depends on the component to be taken up and its properties. For example, pharmaceutical active ingredients are frequently used in the form of a salt, which is generally soluble in water. Water-soluble active ingredients can therefore be employed as aqueous solution or, preferably, be taken up in the aqueous solution or dispersion of the binder. A corresponding statement applies to active ingredients which are soluble in one of the solvents mentioned if the liquid form of the components used is based on an organic solvent.

It is possible where appropriate to replace the softening by dissolving, suspending or dispersing in the abovementioned solvents, if desired and/or necessary with the addition of suitable ancillary substances such as emulsifiers. The solvent is then generally removed to form the plastic mixture in a suitable apparatus, e.g. a kneading and plasticating device. This will be comprised by the term mixing hereinafter.

The softening and mixing take place under conditions of temperature and shear energy input such that the reduction in molecular weight of the polymeric binder, expressed as difference in the K value, is less than 15. The device used for this purpose must be selected on this basis. Twin screw extruders conventionally used for melt extrusion are usually unsuitable. The linking of the melting and mixing step in the extruder requires, in order to bring about adequate mixing, a relatively long residence time in a zone with high shear. This may result in local overheating and an excessive reduction in the molecular weight of the binder. It must also be borne in mind that, to avoid damage to the polymeric binder, the temperature cannot be increased indefinitely. However, the polymeric binders with a K value of more than 80 which are employed according to the invention have a very high viscosity at comparatively low temperatures. Twin screw extruders may be prone to blockage under these conditions.

It has emerged that the process according to the invention can advantageously be carried out in a continuously operating kneader. Preferred kneaders have a shaft which is provided with a screw flight in a cylindrical housing, and the shaft executes an axial movement to and fro in addition to the rotational movement about its own axis. The screw flight preferably has a plurality of interruptions, and the housing has fixed kneading cogs which pass through the interruptions during the movement of the shaft to and fro. Continuously operating kneaders of this type are supplied by Buss under the name Ko-kneader.

The charging of the mixing and plasticizing device takes place continuously or batchwise, according to its design, in a conventional way. Powdered components can be introduced in a free feed, e.g. via a weigh feeder. Plastic compositions can be put in directly or via a gear pump, which is advantageous in particular when the viscosities and pressures are high. Liquid media can be metered in through a suitable pump unit.

The mixture obtained by mixing and/or softening the binder, the active ingredient and, where appropriate, the additive or additives is usually party to viscous (plastic). The glass transition temperature of the mixture is below the decomposition temperature of all the components present in the mixture. The binder should preferably be soluble or swellable in a physiological medium.

The process steps of mixing and softening can be carried out in the same apparatus or in two or more separately operating devices. The preparation of a premix can be carried out in one of the conventional mixing devices described above. Such a premix can then be fed directly, for example, into a continuous kneader and then be extruded, where appropriate with addition of further components.

It is also possible according to the invention to produce multilayer pharmaceutical forms by coextrusion, in which case a plurality of mixtures of the components described above are fed together in extrusion die so that the required layer structure of the multilayer pharmaceutical form results. It is preferred to use different binders for different layers, employing in one layer a binder with a K value of more than 75.

Multilayer drug forms preferably comprise two or three layers. They can be in open or closed form, in particular as open or closed multilayer tablets.

At least one of the layers contains at least one pharmaceutical active ingredient. It is also possible to include another active ingredient in another layer. This has the advantage that two mutually incompatible active ingredients can be processed or that the release characteristics of the active ingredient can be controlled.

The shaping takes place by coextrusion, with the mixtures from the individual extruders or other units being fed through a common coextrusion die. The shape of the coextrusion dies depends on the required pharmaceutical form. For example, dies with a flat orifice, called slot dies, and dies with an annular orifice are suitable. The design of the die depends on the polymeric binder used and the required pharmaceutical form.

The resulting mixture is preferably solvent-free, i.e. it contains neither water nor an organic solvent.

The plastic mixture is usually subjected to a definitive shaping. This may produce a large number of forms depending on the die and mode of shaping. For example, on use of an extruder, the extrudate can be shaped between a belt and a roll, between two belts or between two rolls, as described in EP-A-358 105, or by calendering in a calendar with two molding rolls, see, for example, EP-A-240 904. Further forms can be obtained by extrusion and hot or cold cut of the extrudate, for example small-particle and uniformly shaped pellets. Hot-cut pelletization usually results in lenticular dosage forms (tablets) with a diameter of from 1 to 10 mm, whereas cold-cut pelletization normally leads to cylindrical products with a length to diameter ratio of from 1 to 10 and a diameter of from 0.5 to 10 mm. It is thus possible to produce monolayer, but on use of coextrusion also open or closed multilayer dosage forms, for example oblong tablets, coated tablets, pastilles and pellets. The resulting pellets can then also be ground to powders and compressed to tablets in a conventional way. Micropastilles can be produced by the Rotoform-Sandvik process. These dosage forms can be rounded and/or provided with a coating by conventional methods in a downstream process step. Examples of materials suitable for film coatings are polyacrylates such as Eudragit types, cellulose esters such as hydroxypropylcellulose phthalates, and cellulose ethers such as ethylcellulose, hydroxypropylmethylcellulose or hydroxypropylcellulose.

It is possible for solid solutions to be formed. The term "solid solutions" is familiar to the skilled worker, for example from the literature cited at the outset. In solid solutions of active ingredients in polymers, the active ingredient is in the form of a molecular dispersion in the polymer.

The following examples are intended to illustrate the process according to the invention without restricting it, however.

EXAMPLES

Example 1

Polyvinylpyrrolidone (powder) with a K value of 90, which was mixed with 20% by weight of ibuprofen, was extruded in a BussMDK 46 Ko-kneader from Buss AG, Switzerland. The shaft used had feed sections with continuous screw flight and kneading sections with interrupted screw flight and fixed kneading cogs alternately. The polyvinylpyrrolidone was fed into the last third of the shaft. The temperature was controlled so that it rose from 80° C. at the entry point to 195° C. at the exit point. The extrudate was rapidly brought to room temperature by means of cooling rolls and a cooling belt. The extrudate showed no discoloration and had a K value of 84.5.

Example 2

A mixture of polyvinylpyrrolidone with a K value of 90, 1% by weight of stabilizer (butylhydroxytoluene) and 20% by weight of ibuprofen was extruded as described in Example 1. The extrudate showed no discoloration and had a K value of 85.5.

Comparative Example

A mixture of 85% by weight of polyvinylpyrrolidone with a K value of 90 and 15% by weight of Lutrol 1500 (polyethylene glycol) was extruded in a Werner and Pfleiderer ZSK 30 twin screw extruder. The temperature was 80 to 205° C. The extrudate showed a brown discoloration and had a K value of 60.

We claim:
1. A process for producing solid dosage forms, in which
   (i) a plastic mixture of at least one pharmacologically acceptable polymeric binder with a K value of more than 75, at least one pharmaceutical active ingredient and, where appropriate, pharmaceutical additive is prepared and
   (ii) the plastic mixture is shaped to the required dosage form, with step (i) being carried out under conditions of temperature and shear energy input such that the reduction in molecular weight of the polymeric binder, expressed as the difference in the K value, is less than 15 wherein the polymeric binder is a homo- or copolymer.
2. A process as claimed in claim 1, wherein the polymeric binder is a homo- or copolymer of vinylpyrrolidone.
3. A process as claimed in claim 1, wherein the temperature in step (i) is not more than 250° C.
4. A process as claimed in claim 1, wherein step (i) is carried out in a continuously operating kneader.
5. A process as claimed in claim 4, wherein the kneader has a shaft provided with a screw flight in a cylindrical housing, and the shaft executes an axial movement to and fro in addition to the rotational movement around its own axis.

6. A process as claimed in claim 5, wherein the screw flight has multiple interruptions, and the housing has fixed kneading cogs, with the kneading cogs passing through the interruptions during the movement to and fro of the shaft.

7. A process as claimed in claim 1, wherein the plastic mixture comprises at least one plasticizer.

8. A process as claimed in claim 1, wherein the plastic mixture comprises at least one antioxidant.

* * * * *